(12) United States Patent
Kähkönen

(10) Patent No.: US 6,523,395 B1
(45) Date of Patent: Feb. 25, 2003

(54) METHOD AND MEASURING APPARATUS FOR MEASURING FREENESS

(75) Inventor: Martti Kähkönen, Sotkamo (FI)

(73) Assignee: Metso Automation Oy, Helsinki (FI)

( * ) Notice: Subject to any disclaimer, the term of this patent is extended or adjusted under 35 U.S.C. 154(b) by 0 days.

(21) Appl. No.: 09/743,160

(22) PCT Filed: Jul. 6, 1999

(86) PCT No.: PCT/FI99/00598

§ 371 (c)(1),
(2), (4) Date: Feb. 13, 2001

(87) PCT Pub. No.: WO00/02032

PCT Pub. Date: Jan. 13, 2000

(30) Foreign Application Priority Data

Jul. 7, 1998 (FI) .............................................. 981559 U

(51) Int. Cl.[7] .............................................. G01N 33/34
(52) U.S. Cl. ...................... 73/53.04; 73/54.01; 73/53.03
(58) Field of Search ............................. 73/54.01, 53.03, 73/53.04

(56) References Cited

U.S. PATENT DOCUMENTS

| | | |
|---|---|---|
| 2,602,325 A | 7/1952 | Campbell et al. |
| 4,024,754 A | 5/1977 | Alfthan |
| 4,406,159 A * | 9/1983 | Yanishevsky ............... 73/53.04 |
| 5,026,455 A | 6/1991 | Lehtikoski et al. |
| 5,340,442 A | 8/1994 | Gess et al. |
| 5,365,775 A | 11/1994 | Penniman |
| 5,954,922 A * | 9/1999 | Ramarao ..................... 162/198 |
| 6,018,989 A | 2/2000 | Kubbillum |

FOREIGN PATENT DOCUMENTS

| | | |
|---|---|---|
| DE | 196 35 318 A1 | 3/1998 |
| FI | 5113 | 6/1976 |
| FI | 80342 | 1/1990 |
| GB | 2 001 117 A | 1/1979 |

OTHER PUBLICATIONS

Freeness of Pulp; pp. 1–6; T 227 om–85; Pulp Properties Committee.
Scandinavian Pulp, Paper and Board; SCAN–C19:65; 1964; pp. 1–5.

* cited by examiner

Primary Examiner—Hezron Williams
Assistant Examiner—André K. Jackson
(74) Attorney, Agent, or Firm—Alston & Bird LLP

(57) ABSTRACT

The invention relates to a method and measuring apparatus for measuring freeness. Freeness is measured with the help of an automatic data processing apparatus (30) so that the flow rate of a liquid draining from a measuring chamber (10) is measured using the measuring apparatus (12) until the flow rate is equal to or lower than a predefined flow rate.

25 Claims, 2 Drawing Sheets

METHOD AND MEASURING APPARATUS FOR MEASURING FREENESS

FIELD OF THE INVENTION

The invention relates to a method for measuring freeness, in which method a measuring chamber comprising a wire or the like arranged on the bottom surface of the measuring chamber is filled with a suspension to be measured and the suspension is allowed to flow through the wire or the like at a time instant T0.

The invention further relates to a measuring apparatus to measure freeness, which measuring apparatus comprises a measuring chamber comprising a top lid and a bottom surface shutter that tightly seal the measuring chamber, an air valve and a wire or the like; in the beginning of the measuring process, the measuring chamber contains the suspension to be measured; the shutter of the measuring chamber bottom surface is made to be opened; the measuring apparatus is adapted to allow the suspension to flow through the wire or the like at a time instant T0.

BACKGROUND OF THE INVENTION

To make good quality paper, the properties of paper stock must be precisely measured and controlled. In measuring the freeness of paper stock, the speed with which the paper stock can be separated from water is empirically determined. Freeness depends on several factors, such as fibres, stock processing (for instance mechanical/chemical), the quantity of fines, temperature, consistency, and the measuring apparatus.

One of the most common methods for measuring freeness is CSF (Canadian Standard Freeness). This measuring method is a standard and has been disclosed in detail in publication T 227 om-85, Freeness of pulp, TAPPI, 1985, which is incorporated herein by reference. In the CSF measurement, the freeness of paper stock is measured from a sample with 0.3% consistency and 20° C. temperature. If the consistency or temperature of the sample differs from the specified values, the freeness result is adjusted according to predefined table values so that the measurement corresponds to the specified consistency and temperature values. In the beginning of the CSF measurement, exactly one litre of the sample is measured into a measuring tank comprising the walls of the tank, a top lid that closes against the top part of the walls, a wire at the bottom of the tank, a bottom lid that closes against the bottom part of the walls, and an air valve. The bottom lid is opened and the sample is allowed to settle in the tank so that some of the stock descends on the wire at the bottom of the tank. After approximately 5 s from opening the bottom lid, the air valve is opened so that water starts separating from the stock sample through the wire and the stock piled on the wire. The water flows into a funnel comprising a constant flow spout at the bottom of the funnel and a lateral tube in the bottom section of the funnel. A constant volume (24.2 ml) remains in the funnel between the constant flow spout (constant flow 8.83 ml/s) and the lateral tube. When water flows from the measuring tank into the funnel, part of the water flows out through the constant flow spout, a constant volume (24.2 ml) of water collects between the constant flow spout and the lateral tube and finally some of the water flows out through the lateral tube. In measuring freeness, this volume of water that has flown out through the lateral tube is measured in a measuring glass and this volume of water corresponds to freeness. The measuring is usually performed manually. The measuring method is arduous and sensitive to changes in temperature and consistency. The measuring method is also inaccurate with low CSF values.

Another known method for defining freeness is the Schopper-Riegler method disclosed in publication SCAN-C 19:65, Scandinavian pulp, paper and board, Testing committee, approved 1964, which is incorporated herein by reference. According to this standard method, a known quantity of paper stock is first poured on a spreader cone which is opened after a predefined period of time (5 s), the stock is filtered through a wire and a mat of fibre piling on the wire into a funnel with an orifice at the bottom and the side. Water flows out through the bottom orifice at a constant flow rate [1000 ml/(149 s±1)≈6.71 ml/s]. A constant volume (7.5 ml–8.0 ml) remains between the bottom orifice and the side orifice. The volume of water flowing through the side orifice corresponds to freeness measured in SR units so that 0 ml corresponds to 100 SR units, 1000 ml corresponds to 0 SR units and thus one SR unit corresponds to 10 ml. The SR and CSF scales are reversed in relation to each other, i.e. the highest SR value corresponds to the lowest CSF value. This measuring is also usually performed manually. The measuring method is arduous and sensitive to changes in temperature and consistency. The SR measuring method is also inaccurate with extreme values.

Patent publication U.S. Pat. No. 2,602,325, which is incorporated herein by reference, discloses a method for measuring freeness similar to CSF measuring, in which freeness is determined by measuring the time that elapses when a predefined volume of liquid separates from a suspension in a measuring chamber. Alternatively, it is possible to measure the volume of liquid that separates from a suspension in a measuring chamber during a predefined time. This solution provides the disadvantage of being slow and susceptible to human error.

Freeness can also be measured with an automated measuring apparatus which resembles CSF measuring in principle, but uses vacuum. A sampling apparatus of the measuring apparatus takes a sample of paper stock, and water is added to the sample so that its consistency becomes approximately 3%. The temperature of the sample is measured and the sample is allowed to descend and settle on the wire for 5 seconds. After this, the water is drained from the tank through the wire using vacuum. After a certain period of time, the pressure difference caused by the cake piled on the wire is measured. After the pressure difference has been measured, the consistency of the paper stock is measured using the mass of the cake. Freeness can be calculated from the pressure difference. The disadvantage of this measuring method is that pattern making (calibration) is arduous and difficult, because the apparatus must be calibrated separately for each stock type.

Patent publication FI 80 342, which is incorporated herein by reference, also discloses an automated method and apparatus for defining the dry stuff, freeness and wire retention of pulp. The measuring of freeness is based on measuring the liquid level of a suspension in a measuring chamber as a function of time. The drainage rate is formed as a function of the mass of the dry stuff cake. The measuring requires a precise weighing machine so as to avoid errors in the freeness result. A weighing machine also increases the manufacturing costs of the apparatus.

Patent publication FI 51 133, which is incorporated herein by reference, discloses another automated method and apparatus for measuring freeness by directing pressurized water through a layer of stock and determining the freeness resistance by the volume of water that flows through during a certain period of time. The disadvantage of this measuring method, too, is that calibration is arduous and difficult, because the apparatus must be calibrated separately for each stock type. Pressurized measuring differs from standard measuring and the results are thus not comparable.

BRIEF DESCRIPTION OF THE INVENTION

It is an object of the invention to solve the above-mentioned problems by implementing a method and an apparatus implementing the method. This object is achieved by a method described in the introduction and characterized in that in the method, when the flow starts at a time instant T0, the decrease in the suspension in the measuring chamber is measured as a function of time; a time instant T1 is searched for, at which the decrease in the suspension substantially corresponds to a previously known flow rate $v_c$; and freeness F is determined as a function of the volume of suspension drained from the measuring chamber by the time instant T1.

The measuring apparatus of the invention is characterized in that it comprises a measuring sensor for measuring the drainage of a liquid from a measuring chamber through a wire or the like as a function of time; the measuring apparatus comprises an automatic data processing apparatus to which the sensor is made to feed its measuring data; the automatic data processing apparatus is adapted to search for a time instant T1 at which the drainage of the liquid from the measuring chamber substantially corresponds to a previously known flow rate $v_c$; and the automatic data processing apparatus is adapted to determine freeness F as a function of the volume of suspension drained from the measuring chamber by the time instant T1.

The method and system of the invention provide several advantages. Measuring freeness becomes faster, more accurate and simple. Measuring does not require calibration and the measuring apparatus need not be set to the type of stock used in measuring. Further, repeatability improves, as the human factor involved in the measuring can be minimized. The measuring apparatus of the invention is also inexpensive and quick to take into use.

BRIEF DESCRIPTION OF THE DRAWINGS

In the following the invention will be described in greater detail in connection with preferred embodiments and with reference to the attached drawings, in which.

DETAILED DESCRIPTION OF THE INVENTION

The solution of the invention is especially suitable for paper industry, but is not restricted to it.

Let us first briefly examine the method of the invention. In the solution of the invention the volume of a liquid in a measuring chamber is monitored as a function of time from a time instant T0. When the derivative of the volume of the liquid in relation to time, which corresponds to the flow rate of the liquid draining from the measuring chamber through a wire, reaches a predefined value $v_c$ at a time instant T1, a total volume of liquid $V_{total}$ drained from the measuring chamber up till then, i.e. between T1 and T0, is calculated. A volume $V_{cf}$ that would correspondingly have drained during the same time T1 to T0 through a constant flow spout, i.e. $V_{cf}=v_c*(T1-T0)$, is subtracted from the total volume $V_{total}$. In the CSF method, constant flow $v_c$ is 8.83 ml/s and in the SR method, $v_c$ is 6.71 ml/s, i.e. more specifically 1000 ml/$T_{vc}$, where $T_{vc}$ is 149 s±1 s. Additionally, a constant volume, which corresponds to a threshold value state $V_{th}$ between a constant flow spout and a lateral tube of a lower funnel, is subtracted from the total volume. In the CSF method, the threshold value state is $V_{th}$=24.2 ml and in the SR method, it is $V_{th}$=7.5 to 8.0 ml. Thus according to the method of the invention, freeness F is a function of the differences $V=V_{total}-V_{cf}-V_{th}$, i.e. F=f(V), which corresponds to CSF and SR standard measuring. The CSF result directly and substantially corresponds to the difference result V, i.e. F=V. In calculating freeness F, it is, however, also possible to use some other suitable function based on practical experience. In the SR method, the SR scale increases in a different direction than in the CSF method, which means that freeness F in the SR method is nearly directly F=(1000 ml−V)/10 or some other suitable function based on practical experience. The dependency between the SR and CSF methods is non-linear due to, for instance different wires and air cocks when a suspension is allowed to flow through a wire. In the method of the invention, it is naturally possible to freely select any required values for the constant flow $v_c$ and the threshold value state $V_{th}$.

Figure 1:
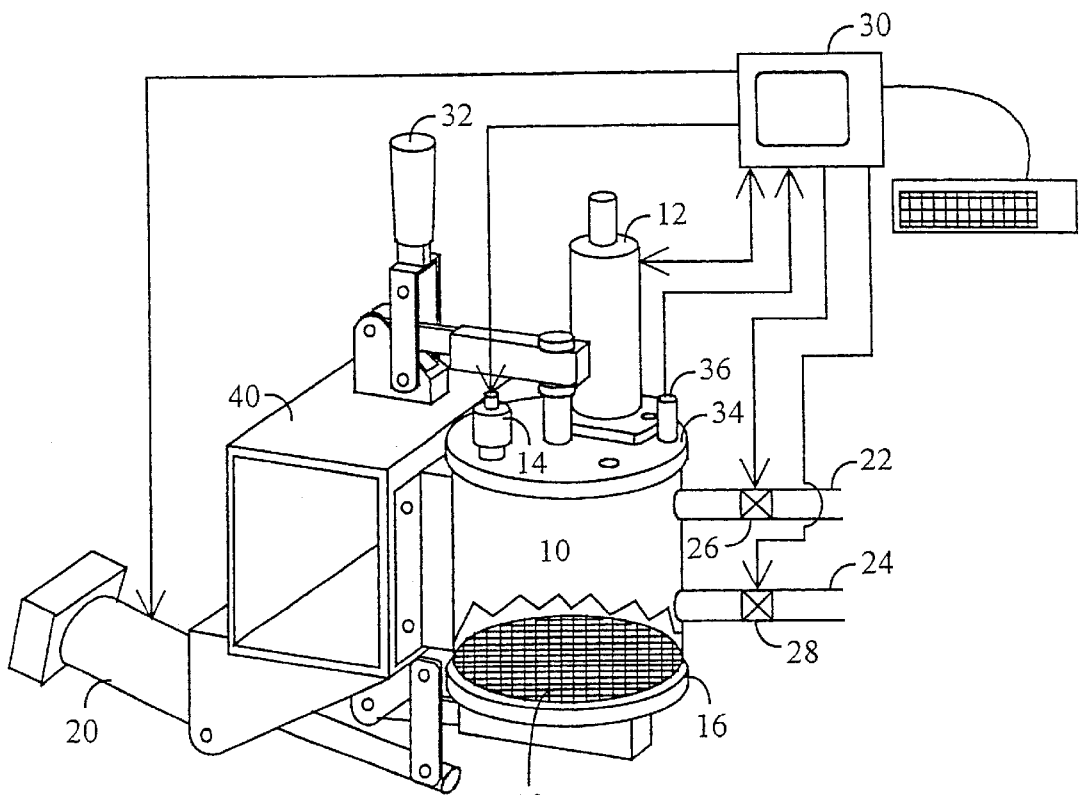
FIG. 1 shows a method of the invention.

Let us now examine the method of the invention using FIG. 1. The measuring apparatus of the invention implementing the method of the invention comprises a measuring chamber 10 comprising a top lid 34 and a bottom lid 16 that tightly seal the measuring chamber 10, and an air valve 14. The measuring chamber is attached to a supporting structure 40. When measuring is started, the measuring chamber 10 is filled with a suspension to be measured. The filling may be performed manually by opening the top lid 34 with a lever 32 and then pouring the suspension into the measuring chamber 10, or automatically through tube 22. Manual filling is not recommended in industrial processes and thus a manual opening mechanism of the top lid is not essential. When the filling is performed through tube 22, an automatic data processing apparatus 30, which is for instance a computer with a microprocessor, opens a valve 26 and the suspension starts to flow into the measuring chamber 10. When the measuring chamber 10 is full, a bottom lid 16 is opened with an opening mechanism 20. After the bottom lid 16 has been opened, the air valve 14 is opened after a predefined delay, usually 5 s, at a time instant T0. Opening the bottom lid 16, measuring the delay and controlling the opening of the air valve 14 are precisely executed by the automatic data processing apparatus 30. The measuring apparatus comprises measuring means 12 for measuring as a function of time the drainage of the liquid from the measuring chamber after the air valve has been opened. The liquid flows through a wire or perforated plate 18 leaving the solid matter in the suspension on the wire or perforated plate 18. The outflow of the liquid is measured with a sensor 12 comprising, for instance an optical or ultrasonic transmitter-receiver pair. The sensor 12 is connected to the automatic data processing apparatus 30. The measuring is performed, for instance so that the optical or acoustic transmitter sends a measuring signal towards the surface of the suspension, from which the signal is reflected to the optical or acoustic receiver. When the location of the transmitter and receiver and the travel time of the signal from the transmitter to the receiver is known, it is possible to specify the level of the surface. The sensor 12 feeds the measuring data of the signal travel time into the automatic data processing apparatus 30 which specifies the flow rate. The automatic data processing apparatus 30 determines freeness F from the collected measuring data according to the method of the invention.

Figure 2:
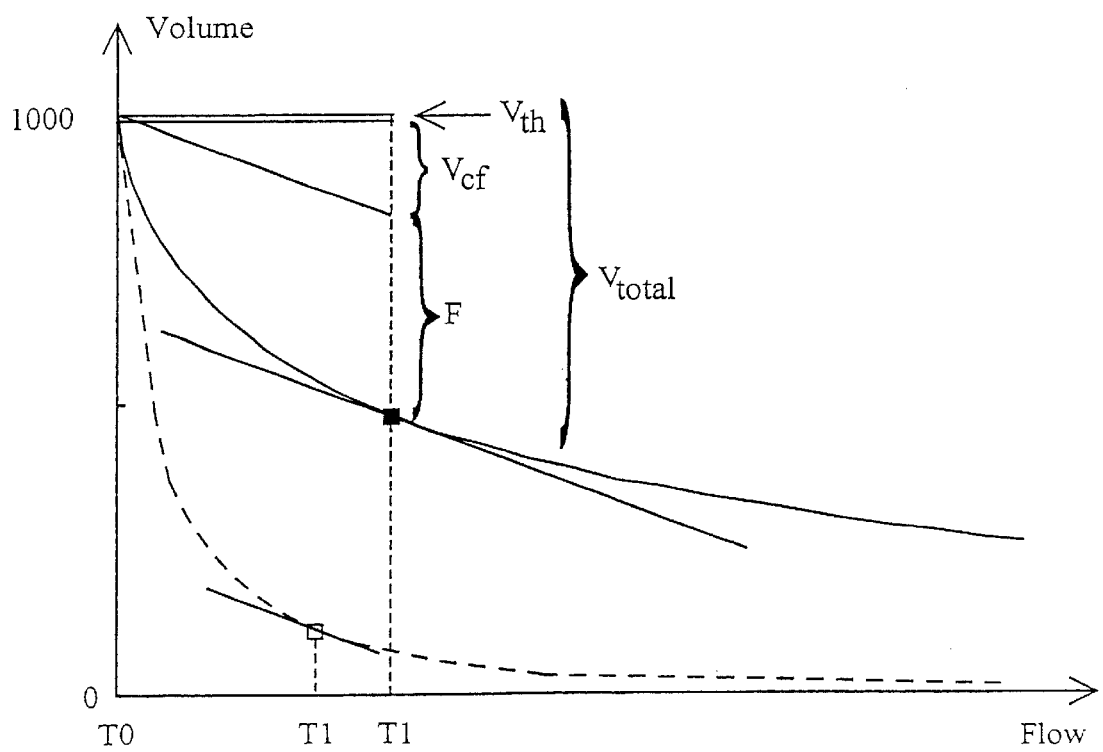
FIG. 2 shows a measuring apparatus of the invention.

Let us now examine the method of the invention using FIG. 2 which shows two curves describing the drainage of the liquid from the measuring chamber 10. In the case of the upper curve, the liquid flows more slowly out of the measuring chamber 10 than in the case of the lower curve (marked with a dash line). The upper curve shows how to read from the curve the total volume $V_{total}$ of drained liquid, the volume flowing out at constant flow $V_{cf}$, freeness F according to the CSF method and the time instant T1, at which the liquid is flowing out from the measuring chamber at a previously known constant flow rate. The lower curve only marks the time instant T1. The slope of the straight line, i.e. the derivative of the curve, shown as the tangent of the curve at the location of the time instant T1 corresponds to the constant flow $v_c$. Typically, the measuring chamber 10 has a capacity of 1000 ml, but the capacity of the measuring chamber 10 is not essential for the solution of the invention. The automatic data processing apparatus 30 searches for, on the basis of the measuring data, a time instant T1, at which the outflow of the liquid from the measuring chamber 10 corresponds substantially to a previously known flow rate $v_c$ which is the constant flow 8.83 ml/s (in the SR method, the constant flow is approximately 6.71 ml/s) of the constant flow spout of the lower funnel preferably used in the CSF standard measuring of freeness. In the CSF standard measuring, when 8.83 ml/s (in the SR method, 6.71 ml/s) of liquid or less flows through the wire, liquid no longer flows from the lateral tube of the lower funnel to the measuring vessel measuring freeness, but the liquid flows out through the constant flow spout. To measure freeness, the automatic data processing apparatus 30 determines, in the solution of the invention, the total volume $V_{total}$, of liquid drained from the measuring chamber 10 from the time when the air valve was opened at the time instant T0 to the time instant T1. The automatic data processing apparatus 30 also calculates the constant flow volume $V_{cf}$ from the time instant T0 to the time instant T1 so that the constant flow $V_{cf}$ is $V_{cf}=V_c*(T1-T0)$. In the CSF standard measuring, the constant flow volume $V_{cf}$ corresponds to the volume of liquid flown through the constant flow spout. The automatic data processing apparatus 30 calculates freeness F of the suspension by subtracting the constant flow volume $V_{cf}$ and the previously known threshold volume $V_{th}$ from the total volume $V_{total}$ of liquid drained from the measuring chamber 10. For instance, freeness F of the CSF method corresponds directly and substantially to the difference result $V=F=V_{total}-V_{cf}-V_{th}$. The method of the invention is suitable for measuring freeness according to both the CSF standard and the SR standard. When the measuring has been performed, the measuring chamber can be cleaned, for instance with pressurized water through a tube 24 when its shutter 28 is opened. The opening of the shutter 28 is preferably controlled by the data processing apparatus 30 which, in the solution of the invention, also measures the temperature of the suspension with a thermometer 36. The data processing apparatus also preferably measures the consistency of the suspension. The consistency and temperature of the suspension being measured in the measuring chamber is controlled by the data processing apparatus 30. The consistency is preferably 0.3% and the temperature 20° C. When the temperature and the consistency differ from the specified values, the data processing apparatus 30 corrects the freeness result correspondingly according to the CSF standard table. The data processing apparatus 30 is connected or integrated to the data network or control system of the process.

Figure 3:
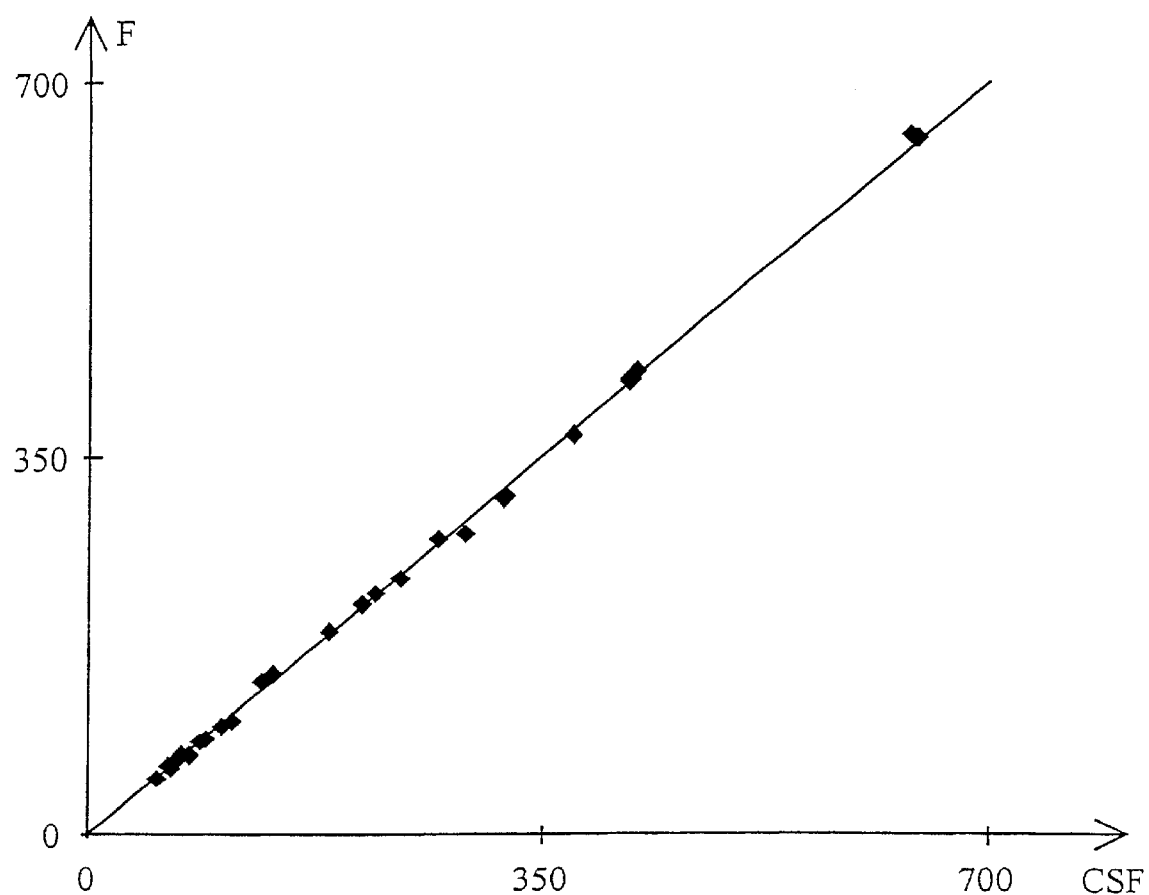
FIG. 3 shows a freeness measuring method of the invention in relation to a standard measuring method.

FIG. 3 shows the freeness results F measured with a measuring apparatus of the invention on the vertical axis and the freeness results CSF according to the CSF standard on the horizontal axis. Freeness has been measured extensively between 50 and 650. The correlation of the results is almost exactly one, i.e. the solution of the invention produces freeness results very closely corresponding to the CSF standard measurements. In fact, the small differences in the results are caused by errors in the CSF standard measuring. As the CSF standard measuring is performed manually, small errors occur easily, for instance in measuring time (5 s), opening the bottom lid and reading the measuring results, whereas the measuring of the invention is fully automated and performed in exactly the same way every time.

Although the invention is described herein with reference to examples in accordance with the accompanying drawings, it is obvious that the invention is not to be so limited, but the invention may be modified in a variety of ways within the scope of the inventive idea disclosed in the appended claims.

What is claimed is:

1. A method for measuring freeness, comprising:
   introducing a suspension to be measured into a measuring chamber having a wire arranged adjacent a bottom of the measuring chamber;
   allowing liquid of the suspension to begin to flow out of the measuring chamber through the wire at a time instant T0;
   measuring a decrease of volume of the suspension in the measuring chamber as a function of time after the flow starts at the time instant T0;
   searching for a time instant T1 at which the decrease in the volume of suspension in the measuring chamber substantially corresponds to a predetermined flow rate $v_c$; and
   calculating freeness F as a function of the volume of suspension drained from the measuring chamber between the time instant T0 and the time instant T1.

2. A method as claimed in claim 1, wherein to calculate freeness F as a function of the volume of suspension drained by the time instant T1:
   a total volume $V_{total}$ drained from the measuring chamber is determined from the time instant T0 to the time instant T1;
   a constant flow volume $V_{cf}$ is calculated from the time instant T0 to the time instant T1 based on the predetermined flow rate $v_c$;
   a difference result V is calculated by subtracting the constant flow volume $V_{cf}$ and a predetermined threshold volume $V_{th}$ from the total volume $V_{total}$ of liquid drained from the measuring chamber, and freeness F of the suspension is calculated as a function of the difference result V.

3. A method as claimed in claim 1, wherein a flow rate of the suspension draining from the measuring chamber is continually measured until the flow rate substantially corresponds to the predetermined flow rate $v_c$ or is lower than $v_c$.

4. A method as claimed in claim 1, wherein temperature of the suspension is measured and freeness F is adjusted according to the temperature.

5. A method as claimed in claim 4, wherein adjustment of the freeness F for temperature is performed according to a standard table.

6. A method as claimed in claim 1, wherein consistency of the suspension is measured and freeness is adjusted according to the consistency.

7. A method as claimed in claim 6, wherein adjustment of the freeness for consistency is performed according to a standard table.

8. A method as claimed in claim 1, wherein volume of the suspension in the measuring chamber is measured by acoustically measuring a height of the upper surface of the suspension in the measuring chamber.

9. A method as claimed in claim 1, wherein volume of the suspension in the measuring chamber is measured by optically measuring a height of the upper surface of the suspension in the measuring chamber.

10. A method as claimed in claim 1, wherein time and volume measurements and calculation of freeness are performed automatically using microprocessor control.

11. A method as claimed in claim 2, wherein the predetermined flow rate is $v_c$=8.83 ml/s and the predetermined threshold volume is $V_{th}$=24.2 ml and freeness F is substantially F=V.

12. A method as claimed in claim 2, wherein the predetermined flow rate is $v_c$=1000 ml/(149 s±1 s) and the predetermined threshold volume is $V_{th}$=7.5–8.0 ml and freeness F is substantially F=(1000 ml–V)/10.

13. A method as claimed in claim 1, wherein the suspension to be measured remains in the measuring chamber for a predefined time before being allowed to begin to flow through the wire.

14. A method as claimed in claim 13, wherein the predefined time is 5 s.

15. A measuring apparatus for measuring freeness, comprising:
- a measuring chamber for containing a quantity of a suspension to be measured, the measuring chamber comprising a top lid and a bottom wall that tightly seal the measuring chamber, an air valve, and a wire arranged adjacent a bottom end of the measuring chamber such that liquid of the suspension will drain from the measuring chamber through the wire when the bottom wall is opened and the air valve is opened;
- a measuring sensor for measuring volume of the liquid drained from the measuring chamber through the wire as a function of time; and
- an automatic data processing apparatus coupled with the sensor and operable to search for a time instant T1 at which the volume of the liquid drained from the measuring chamber substantially corresponds to a predetermined flow rate $v_c$ stored in the automatic data processing apparatus, and further operable to determine freeness F as a function of the volume of suspension drained from the measuring chamber between a time instant T0 at which the suspension first begins to drain from the measuring chamber and the time instant T1.

16. A measuring apparatus as claimed in claim 15, wherein the automatic data processing apparatus is operable to calculate a total volume $V_{total}$ of liquid drained from the measuring chamber from the time instant T0 to the time instant T1, to calculate a constant flow volume $V_{cf}$ from the time instant T0 to the time instant T1 based on the predetermined flow rate $v_c$, to calculate a difference result V by subtracting the constant flow volume $V_{cf}$ and predetermined threshold volume $V_{th}$ from the total volume $V_{total}$ of liquid drained from the measuring chamber, and to calculate freeness F of the suspension as a function of the difference result V.

17. A measuring apparatus as claimed in claim 15, wherein the measuring apparatus is operable to continually measure a flow rate of the liquid draining from the measuring chamber and to determine when the measured flow rate substantially corresponds to the predetermined flow rate $v_c$ or is lower than $v_c$.

18. A measuring apparatus as claimed in claim 15, further comprising a thermometer to measure temperature of the suspension, wherein the thermometer is operable to feed measuring data to the automatic data processing apparatus and the automatic data processing apparatus is operable to adjust freeness according to the temperature.

19. A measuring apparatus as claimed in claim 18, wherein the automatic data processing apparatus is operable to adjust freeness with respect to temperature according to a standard table.

20. A measuring apparatus as claimed in claim 15, wherein the measuring apparatus is adapted to measure consistency of the suspension and the automatic data processing apparatus is operable to adjust freeness according to the consistency.

21. A measuring apparatus as claimed in claim 20, wherein the automatic data processing apparatus is operable to adjust freeness with respect to consistency according to a standard table.

22. A measuring apparatus as claimed in claim 15, wherein the measuring sensor for measuring the volume of the liquid drained from the measuring chamber is operable to acoustically measure a height of the upper surface of the suspension in the measuring chamber.

23. A measuring apparatus as claimed in claim 15, wherein the measuring sensor for measuring the volume of the liquid drained from the measuring chamber is operable to optically measure a height of the upper surface of the suspension in the measuring chamber.

24. A measuring apparatus as claimed in claim 16, wherein the predetermined flow rate is $v_c$=8.83 ml/s and the predetermined threshold volume is $V_{th}$=24.2 ml, and the automatic data processing apparatus is operable to calculate freeness F so that freeness F substantially equals the difference result V.

25. A measuring apparatus as claimed in claim 16, wherein the predetermined flow rate is $v_c$=1000 ml/(149 s±1 s) and the predetermined threshold volume is $V_{th}$=7.5–8.0 ml, and the automatic data processing apparatus is operable to calculate freeness F so that freeness F is substantially F=(1000 ml–V)/10.

* * * * *